United States Patent [19]

Hill et al.

[11] 4,034,077

[45] July 5, 1977

[54] OINTMENTS AND POWDERS CONTAINING SEBACIC ACID

[75] Inventors: John Anthony Hill, New Brunswick; Irwin A. Katz, East Brunswick; John H. Murphy, Toms River, all of N.J.

[73] Assignee: E. R. Squibb & Sons, Inc., Princeton, N.J.

[22] Filed: Jan. 2, 1973

[21] Appl. No.: 320,042

[52] U.S. Cl. .................................. 424/69; 424/365
[51] Int. Cl.$^2$ ...................................... A61K 7/035
[58] Field of Search ........................... 424/365, 69

[56] References Cited

UNITED STATES PATENTS 3,041,289  6/1962  Katchen et al. .............. 424/47 UX

FOREIGN PATENTS OR APPLICATIONS 211,404    1/1957  Australia ........................ 424/365
2,006,345  8/1970  Germany ........................ 424/365

OTHER PUBLICATIONS

Sagarin Cosmetics Science and Technology, 1957, pp. 853–870.
Encyclopedia of Chemical Technology, 1967, vol. 13, pp. 436, 453, 454 and 455.

*Primary Examiner*—Dale R. Ore
*Attorney, Agent, or Firm*—Lawrence S. Levinson; Merle J. Smith; Burton Rodney

[57] ABSTRACT

Baby ointments and diaper powders containing from about 2 to about 30% sebacic acid protect against skin irritation and diaper rash.

11 Claims, No Drawings

OINTMENTS AND POWDERS CONTAINING SEBACIC ACID

OBJECTS OF THE INVENTION

It is an object of the present invention to provide baby ointments and diaper powders which will protect against skin irritation and prevent diaper rash. Another object is to provide baby ointments and diaper powders which neutralize ammonia formed by the action of bacteria on urine. These and other objects of the present invention will be apparent from the following description.

SUMMARY OF THE INVENTION

Baby ointments and diaper powders containing from about 2 to about 30% sebacic acid protect against skin irritation and diaper rash.

DETAILED DESCRIPTION

Bacteria present on the skin are capable of breaking down the urea in urine to form ammonia. This formation of ammonia can burn or irritate the infant's skin, especially when compounded by the chaffing effect of wet diapers. It has now been found that baby ointments and diaper powders containing sebacic acid protect against skin irritation and prevent diaper rash. Physically, sebacic acid is a smooth, palpable powder. Chemically, it is a straight chain dicarboxylic acid containing ten carbon atoms. When present in baby ointments and diaper powders in quantities of from about 2 to about 30% by weight, preferably from about 5 to about 15% by weight, it neutralizes ammonia which may be formed by the action of bacteria on urine. In addition, the sebacic acid acts as a barrier in preventing urine from contacting the baby's skin. The sebacic acid may be employed in microencapsulated form.

The compositions of the present invention also may contain a quaternary ammonium compound which functions as an antibacterial agent to combat bacteria which cause diaper rash. The quaternary ammonium compound may be present in an anti-bacterially effective amount of from about 0.05 to about 1% by weight. Examples of suitable quaternary ammonium compounds are, for example, methyl benzethonium chloride, benzethonium chloride, benzalkonium chloride, and the like.

In addition to the sebacic acid and quaternary ammonium compound, the diaper powder compositions of the present invention also may contain talc or a dry-flow starch which serves to repel moisture and helps keep the skin smooth and dry. The talc or dry-flow starch is employed in a quantity of from about 45 to about 97% by weight. In addition, a small amount, for example, from about 0.1 to about 2% by weight of a hydrophobic silicon dioxide is also present to impart free-flowing properties and to aid in repelling moisture.

The diaper powder compositions of the present invention also may contain from about 20 to about 45% of microencapsulated mineral oil which functions as a liquid emollient when the shell of the capsule is ruptured. Other ingredients such as perfume may be incorporated in quantities sufficient to impart the desired effect.

In addition to the sebacic acid and quaternary ammonium compound, the ointment compositions of the present invention also may contain a liquid emollient such as, for example, acetylated lanolin or cod liver oil. The liquid emollient may be employed in a quantity of from about 1 to about 20% by weight, preferably from about 2 to about 10%.

The ointment also may contain zinc oxide which, in addition to acting as a whitening agent, also imparts astringent properties. The zinc oxide may be present in a quantity of up to about 30% by weight.

In addition, the ointments also may contain a gelled mineral oil or petroleum base in an amount of from about 60 to about 95% by weight. The mineral oil is gelled with a polyalkylene material, e.g., polyethylene. The preparation of such gelled mineral oil is disclosed, for example, in U.S. Pat. Nos. 2,628,187 and 2,627,938. The disclosures of these patents are incorporated by reference. The ointment compositions of the present invention may be prepared in conventional manner by blending the added ingredients into the gelled mineral oil until a uniform mixture is obtained. Other ingredients such as perfume may be incorporated in quantities sufficient to impart the desired effect.

The microcapsules employed herein can be formed of any conventional microencapsulating shell material. The shell material will be self-supporting and may be either water-soluble or water insoluble. The shell material will constitute from about 10 to about 70% by weight of each microcapsule. When the shell material is water insoluble, the shell will be ruptured and the contents released by friction or pressure. When the shell material is water soluble, the contents will be released by contact with moisture, specifically, urine, in addition to the friction or pressure. The microcapsules employed herein can be formed of such materials as urea-formaldehyde or other aminoplast polymer, waxes, fats, proteins, carbohydrates, hydrocolloids, starch derivatives and the like. Such materials and microencapsulating processes are described in detail in one or more of the following U.S. Pat. Nos: 2,183,053; 2,581,441; 2,766,478; 2,799,897; 2,800,457; 2,800,458; 2,911,672; 3,015,128; 3,016,308; 3,137,631; 3,423,489, and 3,516,941. The disclosures of these patents are incorporated herein by reference.

When powders containing such microcapsules are applied as a baby powder, a portion of the microcapsules in the powder can be ruptured, as by pressure of friction, when applying the powder to the skin or to the diaper. While the powder is in contact with the skin a controlled or sustained release is effected by friction due to chafing or rubbing between skin and diaper and, in addition, by moisture in the case of water-soluble shells.

The powder formulations of the present invention may be prepared by mixing the microcapsules with a powder vehicle and other desired additives until an intimate mix is obtained and thereafter discharging the intimate mix into suitable containers. The foregoing mixing step should be carried out under relatively quiescent conditions without employing undue shear which could rupture the microcapsules prematurely.

The following examples illustrate the present invention without, however, limiting the same thereto.

EXAMPLE 1

| Ingredient | OINTMENT % by Weight |
|---|---|
| Methyl benzethonium chloride | 0.1 |

-continued

OINTMENT

| Ingredient | % by Weight |
|---|---|
| Sebacic acid | 10.0 |
| Cod liver oil | 5.0 |
| Acetylated lanolin | 2.0 |
| Perfume | 0.1 |
| Mineral oil gelled with 5% polyethylene (Plastibase 50W) | 82.8 |

EXAMPLE 2

OINTMENT

| Ingredient | % by Weight |
|---|---|
| Methyl benzethonium chloride | 0.1 |
| Sebacic acid | 10.0 |
| Acetylated lanolin | 2.0 |
| Zinc oxide | 20.0 |
| Perfume | 0.075 |
| Mineral oil gelled with 5% polyethylene (Plastibase 50W) | 67.825 |

EXAMPLES 3 – 4

POWDER

| Ingredient | 3 % by Weight | 4 % by Weight |
|---|---|---|
| Talc or dry-flow starch | 96.0 | 71.5 |
| Hydrophobic silicon dioxide (Silanox Cabot) | 0.5 | 0.4 |
| Perfume | 0.3 | 0.2 |
| Sebacic acid | 3.0 | 27.5 |
| Encapsulated methyl benzethonium chloride | 0.2 | 0.4 |

EXAMPLE 5

POWDER

| Ingredient | % by Weight |
|---|---|
| Encapsulated methyl benzethonium chloride | 0.3 |
| Sebacic acid | 13.0 |
| Talc | 86.0 |
| Hydrophobic silicon dioxide (Silanox, Cabot) | 0.5 |
| Perfume | 0.2 |

EXAMPLES 6 – 8

POWDER

| Ingredient | 6 | 7 | 8 |
|---|---|---|---|
| | % by Weight | | |
| Dry flow starch | 54.5 | 48.8 | 58.6 |
| Encapsulated mineral oil | 40.0 | 40.0 | 25.0 |
| Sebacic acid | 5.0 | 10.0 | 15.0 |
| Perfume | 0.2 | 0.2 | 0.2 |
| Hydrophobic silicon dioxide | 0.3 | 1.0 | 1.0 |
| Benzalkonium chloride | — | — | 0.2 |

EXAMPLE 9

POWDER

| Ingredient | % by Weight |
|---|---|
| Dry flow starch | 56.3 |
| Encapsulated mineral oil | 33.0 |
| Encapsulated sebacic acid | 10.0 |
| Perfume | 0.2 |
| Hydrophobic silicon dioxide | 0.3 |
| Benzethonium chloride | 0.2 |

What is claimed is:

1. A powder composition comprising in parts by weight from about 2 to about 30% sebacic acid, from about 45 to about 97% talc, and from about 0.1 to about 2% hydrophobic silicon dioxide.

2. A composition according to claim 1 which additionally contains an anti-bacterially effective amount of a quaternary ammonium compound.

3. A composition according to claim 1 wherein the sebacic acid is encapsulated.

4. A composition according to claim 1 which additionally contains from about 20 to about 45% microencapsulated mineral oil.

5. A composition according to claim 4 wherein the sebacic acid is encapsulated.

6. An ointment composition comprising in parts by weight from about 2 to about 30% sebacic acid, from about 1 to about 20% liquid emollient selected from the group consisting of acetylated lanolin and cod liver oil, and from about 60 to about 95% mineral oil gelled with palyethylene petrolatum base.

7. A composition according to claim 6 which additionally contains an anti-bacterially effective amount of a quaternary ammonium compound.

8. A composition according to claim 6 which additionally contains up to about 30% zinc oxide.

9. A composition according to claim 1 comprising in parts by weight from about 2 to about 30% sebacic acid, from about 65 to about 97% talc, and from about 0.1 to about 2% hydrophobic silicon dioxide.

10. A composition according to claim 1 which contains from about 5 to about 15% sebacic acid.

11. A composition according to claim 6 which contains from about 5 to about 15% sebacic acid.

* * * * *